United States Patent [19]

Schwarz et al.

[11] Patent Number: 4,576,935

[45] Date of Patent: Mar. 18, 1986

[54] DIHALOVINYLPHENYL PHOSPHATES AND THEIR USE AS PESTICIDES

[75] Inventors: Gerd-Ulrich Schwarz, Schifferstadt; Heinrich Adolphi, Limburgerhof, both of Fed. Rep. of Germany

[73] Assignee: BASF Aktiengesellschaft, Fed. Rep. of Germany

[21] Appl. No.: 544,855

[22] Filed: Oct. 24, 1983

[30] Foreign Application Priority Data

Oct. 23, 1982 [DE] Fed. Rep. of Germany ....... 3239288

[51] Int. Cl.$^4$ .......................... A01N 57/06; C07F 9/09
[52] U.S. Cl. .................................... 514/113; 514/128; 514/130; 514/132; 514/134; 558/185; 558/183; 558/191; 558/192; 558/193; 558/195; 558/197; 558/194; 558/99
[58] Field of Search ............... 260/956, 940, 949, 951, 260/954; 514/113, 128, 130, 132, 134

[56] References Cited

FOREIGN PATENT DOCUMENTS 99032 4/1965 United Kingdom .
1449967 9/1976 United Kingdom .

Primary Examiner—Anton H. Sutto
Attorney, Agent, or Firm—Keil & Weinkauf

[57] ABSTRACT

Dihalovinylphenyl phosphates of the formula I

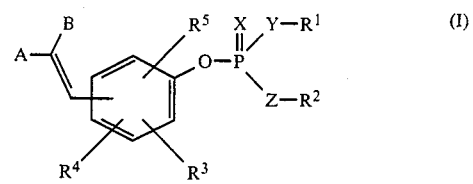

where A and B are each halogen or trihaloalkyl, X is oxygen or sulfur, Y and Z are each oxygen, sulfur or —NH—, $R^1$ is alkyl, $R^2$ is alkyl, haloalkyl, alkoxyalkyl or alkylthioalkyl, and $R^3$, $R^4$ and $R^5$ independently of one another are each hydrogen, halogen, nitro, alkyl, cyano, alkoxy, alkoxyalkoxy, alkylthioalkylthio, alkoxyalkyl, alkylthioalkyl, alkylthio, trihaloalkyl or trihaloalkoxy, and pesticides containing these compounds.

7 Claims, No Drawings

DIHALOVINYLPHENYL PHOSPHATES AND THEIR USE AS PESTICIDES

The present invention relates to dihalovinylphenyl phosphates, a process for their preparation and pesticides which contain these compounds as active ingredients.

It has been disclosed that alkylvinylphenyl phosphates (German Laid-Open Application DOS No. 2,411,809) and halophenylvinyl phosphates (German Laid-Open Application DOS No. 1,567,092) posess insecticidal activity.

We have found that dihalovinylphenyl phosphates of the formula I

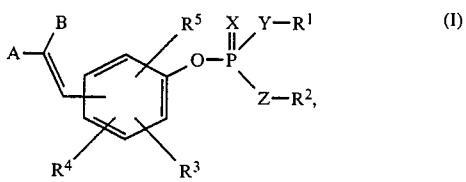

where A and B independently of one another are each fluorine, chlorine or bromine, or trihaloalkyl of 1 to 4 carbon atoms, X is oxygen or sulfur, Y and Z independently of one another are each oxygen, sulfur or the divalent radical —NH—, $R^1$ is alkyl of 1 to 3 carbon atoms, $R^2$ is alkyl, haloalkyl, alkoxyalkyl, alkylthioalkyl of 1 to 6 carbon atoms, and $R^3$, $R^4$ and $R^5$ independently of one another are each hydrogen, halogen, nitro, cyano, alkyl, alkoxy, alkoxyalkoxy, alkylthioalkylthio, alkoxyalkyl, alkylthioalkyl, alkylthio, trihaloalkyl or trihaloalkoxy of 1 to 4 carbon atoms, effectively control pests from the class comprising insects, arachnida and nematodes. Their action is superior to that of the conventional halophenylvinyl phosphates.

The compounds of the formula I can be prepared in a conventional manner, for example by reacting an appropriate phosphoric acid ester halide with an appropriately substituted phenol.

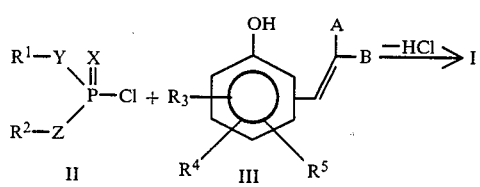

The reaction can be carried out in an organic diluent, eg. acetonitrile, toluene or methyl ethyl ketone, or in a two-phase system, eg. toluene/water or dichloromethane/water.

Advantageously, from 1 to 2 moles of an acid acceptor, ie. a base, are added per mole of phenol, but it is preferable to use an excess of about 10%. Inorganic bases, such as alkali metal carbonates, eg. potassium carbonate, or alkali metal hydroxides, eg. sodium hydroxide, and tertiary amines, eg. triethylamine, are suitable. The base and the phenol can be converted beforehand to the salt, which can be reacted with the phosphoric acid ester chloride. Suitable salts are alkali metal salts, alkaline earth metal salts and unsubstituted or substituted ammonium salts, eg. sodium salts, potassium salts, calcium salts or ammonium salts.

An adequate reaction velocity is achieved in general at below 100° C., preferably from 20° to 70° C., under atmospheric pressure.

The starting materials are advantageously employed in stoichiometric amounts, but an excess of one or other of the reactants may be advantageous in some cases.

The reaction mixture is worked up in a conventional manner, for example by adding water and separating the phases. The crude product can be purified by distillation or column chromatography.

The following methods also give compounds according to the invention: dihalovinylphenyl thiophosphates of the formula Ia can be prepared by subjecting a phosphite of the formula IV to an Arbusow reaction with a sulfenyl chloride of the formula $R^2SCl$, in accordance with the following equation:

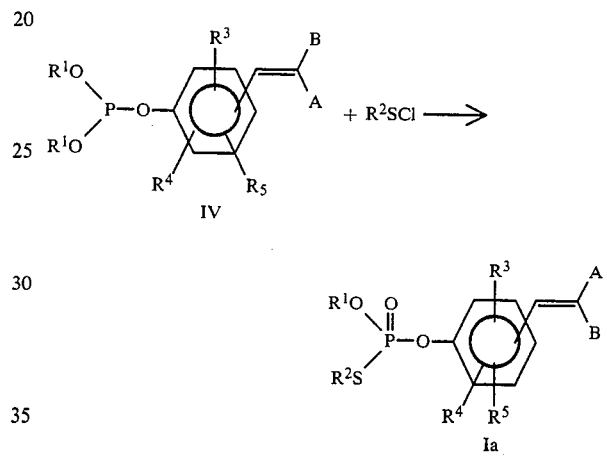

The dihalovinylphenyl thiophosphates of the formula Ia are also obtainable by alkylation of a phosphoric acid ester salt of the formula V with an alkylating agent of the formula $R^2Y$:

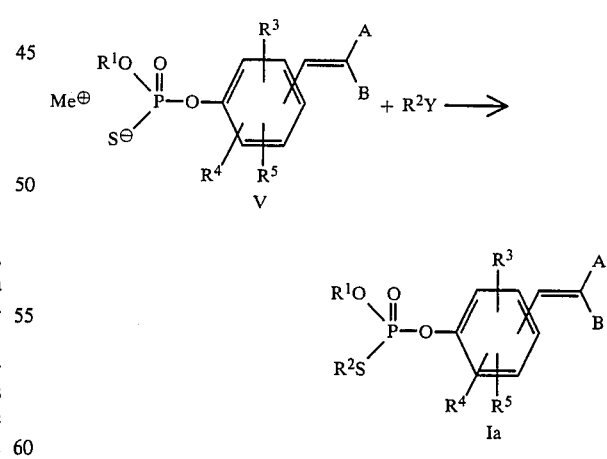

In these formulae, $Me^{\oplus}$ is a cation which is preferably monovalent, eg. $Na^{\oplus}$, $K^{\oplus}$ or $NH_4^{\oplus}$, and Y is halogen or alkylsulfate.

Furthermore, a phosphoric acid ester dichloride of the formula IV can be reacted with an alcohol of the formula $R^1OH$ and a mercaptan of the formula $R^2SH$ to give a compound of the formula Ib:

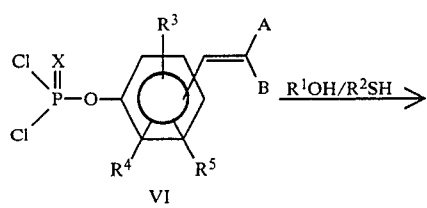

VI

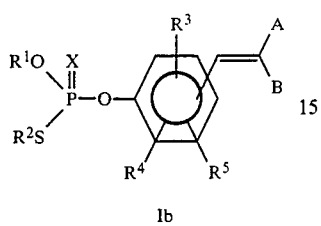

Ib

Dialkyl chlorophosphates are known and can be prepared by a conventional process (German Laid-Open Application DOS Nos. 2,642,982 and 2,552,945, and J. Org. Chem. 30 (1965), 3217).

Dihalovinylphenols of the formula III can also be prepared in a conventional manner.

The reaction below proceeds in the presence of, for example, a Lewis acid, eg., $AlCl_3$:

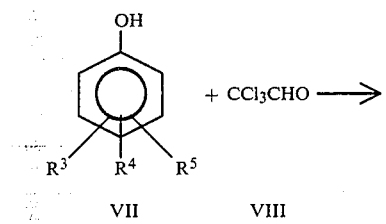

VII    VIII

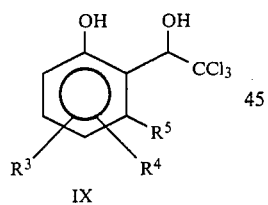

IX

A suitable procedure is described in, for example, SYNTHESIS 1979, 824.

Acetylation of IX, cleavage with zinc in glacial acetic acid (German Laid-Open Application DOS No. 2,633,551) and hydrolysis with NaOH lead, via X and XI, to IIIa:

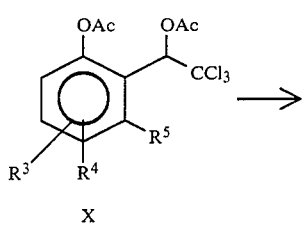

X

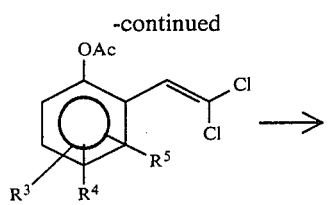

XI

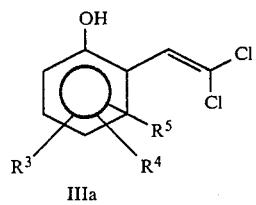

IIIa

The meta- and para-dihalovinylphenols IIIb and IIIc which cannot be obtained in this manner can be obtained if a meta- or para-hydroxybenzaldehyde XII, which is protected with 3,4-dihydropyran, is reacted with, for example, sodium hydride and chloroform to give the compound XIII, this is then acetylated and the protective group is split off with zinc in glacial acetic acid:

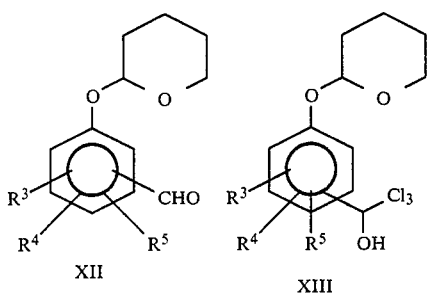

XII        XIII

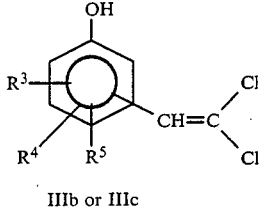

IIIb or IIIc

Another possible method of obtaining compounds of the formula III comprises subjecting an appropriate aldehyde XII to a Wittig reaction with a phosphorylide of the formula XIV:

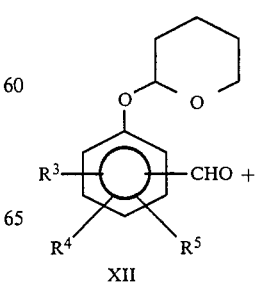

XII

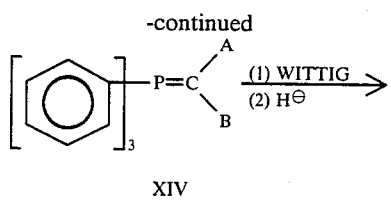

XIV

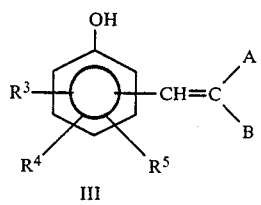

III

Before being further processed to phenyl phosphates, the dihalovinylphenols III, IIIa, IIIb and IIIc can be subjected to other reactions, for example nitration by means of nitric acid.

EXAMPLE OF THE PREPARATION OF O-DIHALOVINYPHENOLS (a) 33.6 g (0.6 mole) of potassium hydroxide and 67 g (0.6 mole) of 4-fluorophenol were dissolved in 300 ml of ethanol, and the solution was evaporated to dryness. The resulting potassium salt was suspended in 1,200 ml of absolute toluene, and 67 g (0.6 mole) of 4-fluorophenol and 79.2 g (0.6 mole) of aluminum chloride were added to the suspension, the aluminum chloride being introduced a little at a time. The mixture was refluxed for 10 minutes, after which it was cooled to below 20° C. and a solution of 177.6 g (1.2 moles) of anhydrous chloral in 600 ml of absolute toluene was gradually added. Stirring was continued overnight, and 1.5 liters of saturated ammonium chloride solution was added, while cooling with ice. The phases were separated, the aqueous phase was extracted three times with toluene, and the extracts were combined, washed and evaporated down. 91 g of 4-fluoro-2-(2,2,2-trichloro1-hydroxyethyl)-phenol of melting point 116°–120° C. (after recrystallization from toluene) were obtained as a crystalline residue.

| Analysis | C | H | Cl | F | O |
|---|---|---|---|---|---|
| calculated | 37.03 | 2.33 | 40.99 | 7.32 | 12.33 |
| found | 37.4 | 2.6 | 41.2 | 7.3 | remainder |

(b) 90 g (0.35 mole) of 4-fluoro-2-(2,2,2-trichloro-1-hydroxyethyl)-phenol were dissolved in 800 ml of absolute ether, and 70 g (0.7 mole) of triethylamine in 500 ml of absolute ether were added. 55 g (0.7 mole) of acetyl chloride in 300 ml of absolute ether were added, a little at a time, at from 0° to 5° C. The mixture was stirred for 3 hours at room temperature, after which it was filtered under suction and the filtrate was evaporated down.

110 g of 4-fluoro-2-(2,2,2-trichloro-1-acetoxyethyl)-acetoxybenzene of melting point 90°–95° C. were obtained as a crystaline residue.

| Analysis | C | H | Cl | F | O |
|---|---|---|---|---|---|
| calculated | 41.42 | 2.73 | 30.96 | 5.53 | 18.63 |
| found | 42.1 | 3.0 | 31.4 | 5.5 | remainder |

(c) 107 g (0.31 mole) of 4-fluoro-2-(2,2,2-trichloro-1-acetoxyethyl)-acetoxybenzene were suspended in 550 ml of glacial acetic acid, and 23.5 g (0.36 mole) of zinc dust were added a little at a time. The mixture was stirred for 6 hours at from 60° to 70° C. and then cooled, the precipitate was filtered off under suction and the filtrate was poured into 1.5 liters of distilled water. This mixture was extracted several times with chloroform, and the extracts were combined, washed with NaHCO$_3$ solution and water, dried and evaporated down.

73 g of 4-fluoro-2-(2,2-dichlorovinyl)-acetoxybenzene of melting point 47°–50° C. were obtained as a crystalline residue.

| Analysis | C | H | Cl | F | O |
|---|---|---|---|---|---|
| calculated | 48.22 | 2.83 | 28.47 | 7.63 | 12.85 |
| found | 47.3 | 2.9 | 29.1 | 7.5 | remainder |

(d) 68 g (0.275 mole) of 4-fluoro-2-(2,2-dichlorovinyl)-acetoxybenzene in 100 ml of absolute ethanol were added to 500 ml of a cold saturated solution of NaOH in ethanol. The mixture was stirred for several hours, after which the pH was brought to 4.7 with acetic acid, while cooling. The mixture was evaporated down (vigorous foaming taking place), the residue was taken up with water and ether, the solution was extracted several times with ether, and the ether extracts were combined, washed with NaHCO$_3$ solution and water, dried over sodium sulfate and evaporated down. 44 g of 4-fluoro-2-(2,2-dichlorovinyl)-phenol of melting point 55°–57° C. were obtained as a crystalline residue.

| Analysis | C | H | Cl | F | O |
|---|---|---|---|---|---|
| calculated | 46.41 | 2.43 | 34.25 | 9.18 | 7.73 |
| found | 46.8 | 2.6 | 34.1 | 9.0 | remainder |

Further processing of a dichlorovinylphenol by introducing a substituent (e) 9.5 g (0.05 mole) of 2-(2′, 2′-dichlorovinyl)-phenol were dissolved in 60ml of acetic anhydride, and a mixture of 6.2 g of 65% strength nitric acid and 6.4 g of concentrated sulfuric acid was added dropwise at 5°–10° C. in the course of 1 hour. The mixture was stirred for two hours at from 10° to 15° C., after which it was poured into 0.5 liters of water and extracted with ether, and the ether extracts were combined, washed with water, dried and evaporated down.

When the residue from evaporation was left to stand for a relatively long time, 10 g of 4-nitro-2-(2,2-dichlorovinyl)-acetoxybenzene of melting point 80°–90° C. were obtained as a crystalline residue.

| Analysis | C | H | N | Cl | O |
|---|---|---|---|---|---|
| calculated | 43.51 | 2.56 | 5.07 | 25.68 | 23.18 |
| found | 43.8 | 2.6 | 4.9 | 25.8 | remainder |

(f) 11 g (0.04 mole) of 4-nitro-2-(2,2-dichlorvinyl)-acetoxybenzene and 50 ml of 4% strength HCl solution were refluxed for 4 hours, while flushing with nitrogen. The mixture was then cooled and extracted three times with ether, and the ether extracts were combined, washed with NaHCO$_3$ solution and water, dried over anhydrous Na$_2$SO$_4$ and evaporated down.

After filtration over silica gel with toluene, 4.0 g of 4-nitro-2-(2,2-dichlorovinyl)-phenol of melting point 107°–115° C. were obtained as a crystalline residue.

| Analysis | C | H | N | Cl | O |
|---|---|---|---|---|---|
| calculated | 41.06 | 2.15 | 5.98 | 30.30 | 20.51 |
| found | 41.2 | 2.1 | 5.9 | 29.9 | 20.7 |

Preparation of m- and p-dichlorovinylphenols (a) 24.4 g (0.2 mole) of 3-hydroxybenzaldehyde were dissolved in 400 ml of absolute tetrahydrofuran, a pinch of p-toluenesulfonic acid was added and 34 g (0.4 mole) of 3,4-dihydropyran were then added dropwise at room temperature. The mixture was stirred for four hours, after which it was washed with ten percent strength potassium hydroxide solution, dried over potassium carbonate and evaporated down in a rotary evaporator. After filtering a solution of the product in toluene over silica gel, 40.0 g of 3-(tetrahydropyranyloxy)-benzaldehyde were obtained in the form of an oil of refractive index $n_D^{20} = 1.5460$.

| Analysis | C | H | O |
|---|---|---|---|
| calculated | 69.89 | 6.84 | 23.27 |
| found | 69.2 | 6.8 | remainder |

(b) A mixture of 27 g (0.13 mole) of 3-(tetrahydropyranyloxy)-benzaldehyde, 17.3 g (0.144 mole) of anhydrous chloroform and 30 ml of tetrahydrofuran was added, a little at a time, to a suspension of 4.6 g (0.144 mole) of sodium hydride in 130 ml of tetrahydrofuran under nitrogen at room temperature, and stirring was continued for 1 hour at 40° C. The mixture was cooled to below 5° C., after which 10.4 g (0.13 mole) of acetyl chloride in 70 ml of tetrahydrofuran were added. The mixture was stirred overnight, water was added and the mixture was extracted with ether. The extracts were washed with an NaHCO₃ solution and water, dried and evaporated down, and the residue was taken up in toluene.

The toluene solution was filtered over silica gel, the toluene was removed and 20 g of crystalline 3-(tetrahydropyranyloxy)-1-(2,2,2-trichloro-1-acetoxyethyl)-benzene of melting point 90°–95° C. were obtained.

| Analysis | C | H | Cl | O |
|---|---|---|---|---|
| calculated | 49.00 | 4.66 | 28.93 | 17.41 |
| found | 49.6 | 4.9 | 28.8 | 17.1 |

(c) 22 g (0.06 mole) of 3-(tetrahydropyranyloxy)-1-(2,2,2-trichloro-1-acetoxyethyl)-benzene were dissolved in 80 ml of glacial acetic acid, 4.6 g (0.07 mole) of zinc dust were added a little at a time, and the mixture was heated at 60°–70° C. for 3 hours. The mixture was cooled and filtered, after which it was introduced into 1.5 liters of water and extracted with ether. The extracts were combined, washed three times with NaHCO₃ solution and water, dried end evaporated down, and the residue was taken up in toluene. The solution was filtered over silica gel, and 8.0 g of 4-dichlorovinylphenol were obtained as a wax-like product.

| Analysis | C | H | Cl | O |
|---|---|---|---|---|
| calculated | 50.83 | 3.20 | 37.51 | 8.46 |
| found | 51.2 | 3.5 | 36.5 | 8.8 |

The examples of (2,2-dihalovinyl)-phenols described in Tables 1, 2 and 3 below were prepared by one of the other methods described above, with appropriate modification of the above practical data; where no physical data are given, the stated compounds were not synthesized; they can be obtained from raw materials having a corresponding constitution.

TABLE 1

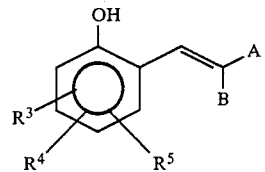

| A | B | R³ | R⁴ | R⁵ | $n_D$/M.p. |
|---|---|---|---|---|---|
| Cl | Cl | 4-Br | H | H | M.p. = 64–67° C. |
| Cl | Cl | H | H | H | M.p. = 47–50° C. |
| Cl | Cl | 4-OCH₃ | H | H | $n_D^{23}$ = 1.5900 |
| Br | Br | 4-F | H | H | $n_D^{22}$ = 1.6195 |
| Cl | Cl | 4-SCH₃ | H | H | $n_D^{20}$ = 1.6458 |
| Cl | Cl | 4-Cl | H | H | M.p. = 61–65° C. |
| Cl | Cl | 4-CH₃ | H | H | M.p. = 42–44° C. |
| Br | Br | H | H | H | |
| F | F | H | H | H | |
| F | F | 4-F | H | H | |
| F | F | 4-F | H | H | |
| Br | Br | 4-Br | H | H | |
| CF₃ | CF₃ | H | H | H | |
| CCl₃ | CCl₃ | H | H | H | |
| F | CCl₃ | H | H | H | |
| Cl | CF₃ | H | H | H | |
| F | CF₃ | H | H | H | |
| Cl | CCl₃ | H | H | H | |
| Br | F | H | H | H | |
| F | Cl | H | H | H | |
| Br | Cl | H | H | H | |
| Cl | Cl | 4-CN | H | H | |

TABLE 2

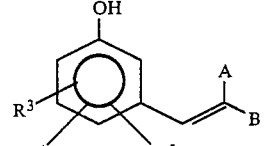

| A | B | R³ | R⁴ | R⁵ | $n_D$/M.p. |
|---|---|---|---|---|---|
| F | F | H | H | H | |
| Br | Br | H | H | H | |
| Cl | Cl | 4-F | H | H | |
| Cl | Cl | 4-Cl | H | H | |
| Cl | Cl | 4-Br | H | H | |
| Cl | Cl | 6-OCH₃ | H | H | |
| F | F | 6-OCH₃ | H | H | |
| Br | Br | 6-OCH₃ | H | H | |
| CF₃ | CF₃ | H | H | H | |
| CCl₃ | CCl₃ | H | H | H | |
| F | CF₃ | H | H | H | |
| F | CCl₃ | H | H | H | |
| Cl | CF₃ | H | H | H | |
| Cl | CCl₃ | H | H | H | |
| Br | F | H | H | H | |
| Br | Cl | H | H | H | |
| F | Cl | H | H | H | |

TABLE 3

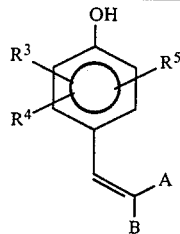

| A | B | R³ | R⁴ | R⁵ | $n_D$/M.p. |
|---|---|---|---|---|---|
| Cl | Cl | H | H | H | M.p. 88–91° C. |
| Cl | Cl | 2-OC$_2$H$_5$ | H | H | |
| Cl | Cl | 3-OCH$_3$ | H | H | |
| Cl | Cl | 2-OCH$_3$ | 6-Br | H | |
| Cl | Cl | 2-Br | 6-Br | H | |
| Cl | Cl | 2-I | 6-I | H | |
| F | F | H | H | H | |
| Br | Br | H | H | H | |
| CF$_3$ | CF$_3$ | H | H | H | |
| CCl$_3$ | CCl$_3$ | H | H | H | |
| CCl$_3$ | F | H | H | H | |
| CCl$_3$ | Cl | H | H | H | |
| CF$_3$ | F | H | H | H | |
| CF$_3$ | Cl | H | H | H | |
| Br | F | H | H | H | |
| F | Cl | H | H | H | |
| Cl | Br | H | H | H | |

EXAMPLE RELATING TO THE MANUFACTURE OF A PHOSPHORIC ACID ESTER ACTIVE INGREDIENT 8.0 g (0.03 mol) of 4-Br-2-(2,2-dichlorovinyl)-phenol were dissolved in 100 ml of methanol, 5.4 g (0.03 mole) of a 30% strength sodium methylate solution in methanol were added, and the mixture was concentrated. The sodium salt was taken up in 100 ml of absolute acetone. 5.0 g (0.031 mole) of O,O-dimethylthiophosphoryl chloride in 10 ml of absolute acetone was dripped into this solution. The mixture was stirred overnight, water was then added, and extraction carried out with ether. The extracts were combined, washed with water, dried and concentrated. Chromatography in a silica gel column using toluene gave 7.2 g of O,O-dimethyl-O-4-Br-2-(2-dichlorovinyl)-phenylthiophosphate (active ingredient no. 1) as an oil having a refractive index $n_D^{23}=1.5900$.

| Analysis | C | H | O | S | Cl | Br | P |
|---|---|---|---|---|---|---|---|
| calc.: | 30.64 | 2.57 | 12.24 | 8.18 | 18.09 | 20.38 | 7.90 |
| found.: | 30.9 | 2.6 | 12.0 | 8.6 | 18.4 | 20.5 | 7.7 |

Where, in Tables 4, 5 and 6 below, physical characteristics (melting point, refractive index) are given, the phosphoric acid esters have been prepared; generally, they have a good or very good insecticidal action. The compounds without any physical data are examples of compounds according to the invention; in view of their structural similarity, they are expected to have a similar action to that of the compounds found to be effective.

The compounds of the following table 4 were, to the extent that physical properties (M.p./$n_D$) are given for them, synthesized by appropriate modification of preceding example. Compounds not characterized by physical constants may be obtained accordingly.

TABLE 4

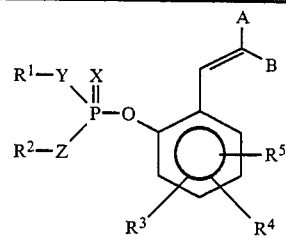

| No. | A | B | X | Y | Z | R¹ | R² | R³ | R⁴ | R⁵ | $n_D$/M.p. |
|---|---|---|---|---|---|---|---|---|---|---|---|
| 2 | Cl | Cl | S | O | O | C$_2$H$_5$ | C$_2$H$_5$ | 4-F | H | H | $n_D^{23}$ = 1.5324 |
| 3 | Cl | Cl | S | O | O | CH$_3$ | CH$_3$ | 4-F | H | H | $n_D^{23}$ = 1.5545 |
| 4 | Cl | Cl | S | O | S | C$_2$H$_5$ | C$_2$H$_5$ | 4-F | H | H | $n_D^{23}$ = 1.5713 |
| 5 | Cl | Cl | S | O | S | C$_2$H$_5$ | C$_3$H$_7$ | 4-F | H | H | $n_D^{23}$ = 1.5658 |
| 6 | Cl | Cl | O | O | S | C$_2$H$_5$ | C$_3$H$_7$ | 4-F | H | H | $n_D^{23}$ = 1.5399 |
| 7 | Cl | Cl | S | N | N | (CH$_3$)$_2$ | (CH$_3$)$_2$ | 4-F | H | H | M.p. = 73–77° C. |
| 8 | Cl | Cl | O | O | S | C$_2$H$_5$ | C$_3$H$_7$ | 4-Br | H | H | $n_D^{23}$ = 1.5722 |
| 9 | Cl | Cl | S | O | O | C$_2$H$_5$ | C$_2$H$_5$ | 4-Br | H | H | $n_D^{23}$ = 1.5683 |
| 10 | Cl | Cl | S | O | S | C$_2$H$_5$ | C$_2$H$_5$ | 4-Br | H | H | $n_D^{23}$ = 1.6018 |
| 11 | Cl | Cl | S | N | N | (CH$_3$)$_2$ | (CH$_3$)$_2$ | 4-Br | H | H | M.p. = 124–130° C. |
| 12 | Cl | Cl | S | O | O | C$_2$H$_5$ | C$_2$H$_5$ | 4-OCH$_3$ | H | H | $n_D^{22}$ = 1.5504 |
| 13 | Cl | Cl | S | O | S | C$_2$H$_5$ | C$_3$H$_7$ | 4-OCH$_3$ | H | H | $n_D^{22}$ = 1.5603 |
| 14 | Cl | Cl | S | O | S | C$_2$H$_5$ | C$_2$H$_5$ | 4-OCH$_3$ | H | H | $n_D^{22}$ = 1.5795 |
| 15 | Cl | Cl | O | O | S | C$_2$H$_5$ | C$_3$H$_7$ | 4-CH$_3$ | H | H | $n_D^{23}$ = 1.5503 |
| 16 | Cl | Cl | S | O | O | C$_2$H$_5$ | C$_2$H$_5$ | 4-CH$_3$ | H | H | $n_D^{23}$ = 1.5465 |
| 17 | Cl | Cl | S | O | O | CH$_3$ | CH$_3$ | 4-CH$_3$ | H | H | $n_D^{23}$ = 1.5629 |
| 18 | Cl | Cl | O | O | S | C$_2$H$_5$ | C$_3$H$_7$ | 4-Cl | H | H | $n_D^{23}$ = 1.5583 |
| 19 | Cl | Cl | S | O | O | C$_2$H$_5$ | C$_2$H$_5$ | 4-Cl | H | H | $n_D^{23}$ = 1.5555 |
| 20 | Cl | Cl | S | O | N | C$_2$H$_5$ | i-C$_3$H$_7$ | 4-Cl | H | H | $n_D^{20}$ = 1.5670 |
| 21 | Cl | Cl | S | O | O | CH$_3$ | CH$_3$ | 4-Cl | H | H | viscous oil |
| 22 | Cl | Cl | O | O | S | C$_2$H$_5$ | C$_3$H$_7$ | H | H | H | $n_D^{23}$ = 1.5575 |
| 23 | Cl | Cl | S | O | N | C$_2$H$_5$ | i-C$_3$H$_7$ | H | H | H | $n_D^{23}$ = 1.5440 |
| 24 | Cl | Cl | S | O | O | C$_2$H$_5$ | C$_2$H$_5$ | H | H | H | $n_D^{26}$ = 1.5466 |
| 25 | Cl | Cl | S | O | O | CH$_3$ | CH$_3$ | H | H | H | $n_D^{26}$ = 1.5674 |
| 26 | Cl | Cl | O | O | S | C$_2$H$_5$ | C$_3$H$_7$ | 4-SCH$_3$ | H | H | $n_D^{20}$ = 1.5812 |
| 27 | Cl | Cl | O | O | S | C$_2$H$_5$ | CH$_3$—O—C$_2$H$_4$ | 4-SCH$_3$ | H | H | $n_D^{20}$ = 1.5771 |
| 28 | Cl | Cl | O | O | S | C$_2$H$_5$ | i-C$_3$H$_7$—O—C$_2$H$_4$ | 4-SCH$_3$ | H | H | $n_D^{23}$ = 1.5650 |
| 29 | Cl | Cl | O | O | S | C$_2$H$_5$ | sec-C$_4$H$_9$ | 4-SCH$_3$ | H | H | $n_D^{20}$ = 1.5695 |

TABLE 4-continued

Structure:
R¹−Y\
R²−Z/P(=X)−O−[phenyl with R³, R⁴, R⁵]−CH=C(A)(B)

| No. | A | B | X | Y | Z | R¹ | R² | R³ | R⁴ | R⁵ | $n_D$/M.p. |
|---|---|---|---|---|---|---|---|---|---|---|---|
| 30 | Br | Br | O | O | S | $C_2H_5$ | i-$C_3H_7$—O—$C_2H_4$ | H | H | H | $n_D^{18} = 1.5637$ |
| 31 | Br | Br | O | O | S | $C_2H_5$ | $C_3H_7$ | H | H | H | |
| 32 | Br | Br | O | O | S | $C_2H_5$ | $C_3H_7$ | 4-Br | H | H | |
| 33 | Br | Br | O | O | S | $C_2H_5$ | $C_3H_7$ | 4-F | H | H | |
| 34 | F | F | O | O | S | $C_2H_5$ | $C_3H_7$ | H | H | H | |
| 35 | F | F | O | O | S | $C_2H_5$ | $C_3H_7$ | 4-F | H | H | |
| 36 | F | F | O | O | S | $C_2H_5$ | $C_3H_7$ | 4-Br | H | H | |
| 37 | Br | Cl | O | O | S | $C_2H_5$ | $C_3H_7$ | 4-Br | H | H | |
| 38 | F | Cl | O | O | S | $C_2H_5$ | $C_3H_7$ | 4-Br | H | H | |
| 39 | Br | F | O | O | S | $C_2H_5$ | $C_3H_7$ | 4-Br | H | H | |
| 40 | $Cl_3$ | $Cl_3$ | O | O | S | $C_2H_5$ | $C_3H_7$ | 4-F | H | H | |
| 41 | $CF_3$ | $CF_3$ | O | O | S | $C_2H_5$ | $C_3H_7$ | 4-F | H | H | |
| 42 | Cl | $CCl_3$ | O | O | S | $C_2H_5$ | $C_3H_7$ | 4-F | H | H | |
| 43 | F | $CCl_3$ | O | O | S | $C_2H_5$ | $C_3H_7$ | 4-F | H | H | |
| 44 | Cl | $CF_3$ | O | O | S | $C_2H_5$ | $C_3H_7$ | 4-F | H | H | |
| 45 | F | $CF_3$ | O | O | S | $C_2H_5$ | $C_3H_7$ | 4-F | H | H | |
| 46 | Cl | Cl | O | O | S | $C_2H_5$ | sec-$C_4H_9$ | 4-$CF_3$ | H | H | |
| 47 | Cl | Cl | O | O | S | $C_2H_5$ | sec-$C_4H_9$ | 4-$CCl_3$ | H | H | |
| 48 | Cl | Cl | O | O | S | $C_2H_5$ | sec-$C_4H_9$ | 4-$OCF_3$ | H | H | |
| 49 | Cl | Cl | S | O | S | $C_2H_5$ | $C_3H_7$ | 4-$NO_2$ | H | H | $n_D^{24} = 1.5910$ |
| 50 | Cl | Cl | O | O | S | $C_2H_5$ | $C_3H_7$ | 4-CN | H | H | |

TABLE 5

Structure:
[phenyl with R³, R⁴, R⁵]−O−P(=X)(Y−R¹)(Z−R²), phenyl substituted with −CH=C(A)(B)

| No. | A | B | X | Y | Z | R¹ | R² | R³ | R⁴ | R⁵ | $n_D$/M.p. |
|---|---|---|---|---|---|---|---|---|---|---|---|
| 51 | Cl | Cl | O | O | S | $C_2H_5$ | $CH_3$—O—$C_2H_4$ | H | H | H | $n_D^{21} = 1.5568$ |
| 52 | Cl | Cl | O | O | S | $C_2H_5$ | sec-$C_4H_9$ | H | H | H | $n_D^{20} = 1.5520$ |
| 53 | Cl | Cl | O | O | S | $C_2H_5$ | $C_3H_7$ | 6-$CF_3$ | H | H | |
| 54 | Cl | Cl | O | O | S | $C_2H_5$ | $C_3H_7$ | 4-$OCF_3$ | H | H | |
| 55 | Br | Br | O | O | S | $C_2H_5$ | $C_3H_7$ | H | H | H | |
| 56 | Br | Br | O | O | S | $C_2H_5$ | $C_3H_7$ | 4-Br | H | H | |
| 57 | Br | Br | O | O | S | $C_2H_5$ | $C_3H_7$ | 2-F | H | H | |
| 58 | F | F | O | O | S | $C_2H_5$ | $C_3H_7$ | H | H | H | |
| 59 | F | F | O | O | S | $C_2H_5$ | $C_3H_7$ | 2-F | H | H | |
| 60 | F | F | O | O | S | $C_2H_5$ | $C_3H_7$ | 2-Br | H | H | |
| 61 | Br | Cl | O | O | S | $C_2H_5$ | $C_3H_7$ | 4-Br | H | H | |
| 62 | F | Cl | O | O | S | $C_2H_5$ | $C_3H_7$ | 4-Br | H | H | |
| 63 | Br | F | O | O | S | $C_2H_5$ | $C_3H_7$ | 4-Br | H | H | |
| 64 | $CCl_3$ | $CCl_3$ | O | O | S | $C_2H_5$ | $C_3H_7$ | 4-F | H | H | |
| 65 | $CF_3$ | $CF_3$ | O | O | S | $C_2H_5$ | $C_3H_7$ | 2-F | H | H | |
| 66 | Cl | $CCl_3$ | O | O | S | $C_2H_5$ | $C_3H_7$ | 2-F | H | H | |
| 67 | F | $CCl_3$ | O | O | S | $C_2H_5$ | $C_3H_7$ | 4-F | H | H | |
| 68 | Cl | $CF_3$ | O | O | S | $C_2H_5$ | $C_3H_7$ | 2-F | H | H | |
| 69 | F | $CF_3$ | O | O | S | $C_2H_5$ | $C_3H_7$ | 4-F | H | H | |
| 70 | Cl | Cl | O | O | S | $C_2H_5$ | sec-$C_4H_9$ | 6-$OCH_3$ | H | H | |
| 71 | Cl | Cl | O | O | S | $C_2H_5$ | i-$C_4H_9$ | H | H | H | |

TABLE 6

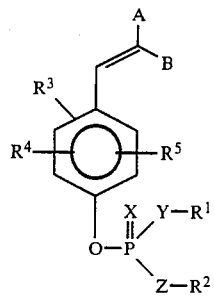

| No. | A | B | X | Y | Z | $R^1$ | $R^2$ | $R^3$ | $R^4$ | $R^5$ | $n_D$/M.p. |
|---|---|---|---|---|---|---|---|---|---|---|---|
| 72 | Cl | Cl | O | O | S | $C_2H_5$ | $C_3H_7$ | H | H | H | $n_D^{23} = 1.5616$ |
| 73 | Cl | Cl | O | O | S | $C_2H_5$ | sec-$C_4H_9$ | H | H | H | $n_D^{23} = 1.5590$ |
| 74 | Cl | Cl | O | O | S | $C_2H_5$ | i-$C_4H_9$ | H | H | H | $n_D^{23} = 1.5558$ |
| 75 | Cl | Cl | O | O | S | $C_2H_5$ | $C_3H_7$ | 2-$CF_3$ | H | H | |
| 76 | Cl | Cl | O | O | S | $C_2H_5$ | sec-$C_4H_9$ | 2-$OCF_3$ | H | H | |
| 77 | Br | Br | O | O | S | $C_2H_5$ | $C_3H_7$ | H | H | H | |
| 78 | Br | Br | O | O | S | $C_2H_5$ | $C_3H_7$ | 2-Br | H | H | |
| 79 | Br | Br | O | O | S | $C_2H_5$ | $C_3H_7$ | 2-F | H | H | |
| 80 | F | F | O | O | S | $C_2H_5$ | $C_3H_7$ | H | H | H | |
| 81 | F | F | O | O | S | $C_2H_5$ | $C_3H_7$ | 2-F | H | H | |
| 82 | F | F | O | O | S | $C_2H_5$ | $C_3H_7$ | 2-Br | H | H | |
| 83 | Br | Cl | O | O | S | $C_2H_5$ | $C_3H_7$ | 2-Br | H | H | |
| 84 | F | Cl | O | O | S | $C_2H_5$ | $C_3H_7$ | 2-Br | H | H | |
| 85 | Br | F | O | O | S | $C_2H_5$ | $C_3H_7$ | 2-Br | H | H | |
| 86 | $CCl_3$ | $CCl_3$ | O | O | S | $C_2H_5$ | $C_3H_7$ | 2-F | H | H | |
| 87 | $CF_3$ | $CF_3$ | O | O | S | $C_2H_5$ | $C_3H_7$ | 2-F | H | H | |
| 88 | Cl | $CCl_3$ | O | O | S | $C_2H_5$ | $C_3H_7$ | 2-F | H | H | |
| 89 | F | $CCl_3$ | O | O | S | $C_2H_5$ | $C_3H_7$ | 2-F | H | H | |
| 90 | Cl | $CF_3$ | O | O | S | $C_2H_5$ | $C_3H_7$ | 2-F | H | H | |
| 91 | F | $CF_3$ | O | O | S | $C_2H_5$ | $C_3H_7$ | 2-F | H | H | |
| 92 | Cl | Cl | O | O | S | $C_2H_5$ | sec-$C_4H_9$ | 3-$OCH_3$ | H | H | |
| 93 | Cl | Cl | O | O | S | $C_2H_5$ | sec-$C_4H_9$ | 2-Br | 6-Br | H | |
| 94 | Cl | Cl | O | O | S | $C_2H_5$ | sec-$C_4H_9$ | 2-I | 2-I | H | |
| 95 | Cl | Cl | O | O | S | $C_2H_5$ | $CH_3-O-C_2H_4$ | H | H | H | |

The above, and other, active ingredients are applied in the manner customary for phosphoric acid esters. Details on formulation, application techniques and mode of action, and details of suitable mixture components for achieving synergistic and other advantageous actions are given for example in U.S. Pat. No. 4,320,122 or the equivalent European Patent Office Publication No. 50,219, which is incorporated herein by reference.

A particularly important area of use for the insecticides-which have a broad range of action-is for combating caterpillars of harmful butterflies listed in the above-mentioned publication.

USE EXAMPLE 1

Contact action on oriental cockroaches (*Blatta orientalis*)

The bottom of 1-liter preserving jars was treated with acetonic solutions of the active ingredients. After the solvent had evaporated, 5 adult cockroaches were introduced into each jar. The kill rate was determined after 48 hours.

In this test, the compounds of Examples 5, 6, 8, 15, 18, 22, 29 and 51 were fully effective at a rate of 0.1 mg or less, i.e., they achieved 100% kill, whereas the comparative agent was insufficiently active. A 100% kill was only achieved by the comparative agent at a rate of 0.25 mg.

USE EXAMPLE 2

Formulations of the active ingredients were added to 200 ml of tapwater; 30 to 40 mosquito larvae of the 4th larval stage were then introduced. The temperature was kept at 20° C. The action was assessed after 24 hours.

In this test, the compounds of Examples 5, 6, 8, 13, 15, 18 and 22 had an action which was at least 5 times better than that of the comparative agent.

USE EXAMPLE 3

Petri dishes 10 cm in diameter were lined with 1 ml of acetonic solutions of the active ingredients. After the solvent had evaporated, 20 larvae in the penultimate stage were placed in the dishes, and the effect was registered after 24 hours.

In this test, the compounds of Examples 6, 8, 18, 22, 27 and 51 has an action which was from twice to 10 times as good as that of the comparative agent.

USE EXAMPLE 4

Contact action and effect of ingested food on caterpillars of the diamondback moth (*Plutella maculipennis*)

Leaves of young cabbage plants were dipped for 3 seconds in aqueous emulsions of the active ingredients, and, after briefly having allowed excess liquid to drip off, were placed on a moist filter paper in a Petri dish. 10 caterpillars in the 4th stage were then placed on the leaves. The action was assessed after 48 hours.

In this test, the compounds of Examples 5, 6, 8, 13, 18, 22, 26 and 51 had an action which was from twice to 10 times as good as that of the comparative agent.

USE EXAMPLE 5

Contact action on bean aphids (*Aphis fabae*), spray experiment

Potted bean plants (*Vicia faba*) with extensive bean aphid colonies were sprayed to runoff in a spray booth with aqueous formulations of the active ingredients. Assessment took place after 48 hours.

In this test, the compounds of Examples 6, 13, 15 and 18 had an action which was at least twice as good as that of the comparative agent.

USE EXAMPLE 6

Action on spider mites (*Tetranychus telarius*)

Potted bush beans which had developed the first pair of true leaves and were under heavy attack from spider mites (*Tetranychus telarius*) of all stages were sprayed to runoff from all sides in a spray cabinet with aqueous formulations of the active ingredients.

The plants were placed on a rotatable disc and were sprayed with 50 ml of spray liquor. Spraying lasted for about 22 seconds. The plants were investigated after 8 days for living spider mites.

In this test, the compounds of Examples 5, 6, 8, 18 and 22 had an action which was from 4 to 20 times better than that of the comparative agent.

USE EXAMPLE 7

Action on root-knot nematodes (*Meloidogyne incognita*)

30 ml of aqueous formulations of the active ingredients was intimately mixed with 300 g of mold heavily infested with *Meloidogyne incognita*. The mold was then filled into plastic pots and a tomato seedling planted therein. The pots were kept under greenhouse conditions at from 22° to 24° C.

The roots were checked for root-knots after 6 to 8 weeks.

In this test, the compounds of Examples 6, 8, 18 and 22 were effective at a concentration of 0.1% or less, whereas the comparative agent was ineffective.

We claim:

1. A dihalovinylphenyl phosphate of the formula

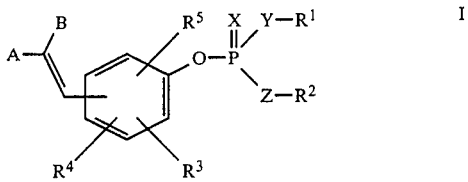

where A and B independently of one another are each fluorine, chlorine and bromine, or trihaloalkyl of 1 to 4 carbon atoms, X is oxygen or sulfur, Y and Z independently of one another are each oxygen, sulfur or the divalent radical —NH—, $R^1$ is alkyl of 1 to 3 carbon atoms, $R^2$ is alkyl, haloalkyl, alkoxyalkyl, alkylthioalkyl of 1 to 6 carbon atoms, and $R^3$, $R^4$ and $R^5$ independently of one another are each hydrogen, halogen, nitro, cyano, alkyl, alkoxy, alkylthio, trihaloalkyl or trihaloalkoxy of 1 to 4 carbon atoms.

2. A method of combating insects which comprises: applying to the insects or their habitat an effective amount of a compound of the formula I as defined in claim 1.

3. A compound of the formula I of claim 1, wherein A and B independently of one another are each chlorine or trichloromethyl.

4. A compound of the formula I of claim 1, wherein A and B are each chlorine.

5. A compound of the formula I of claim 1, wherein A is chlorine and B is trichloromethyl.

6. A compound of the formula I of claim 1, wherein at least 1 of $R^3$ $R^4$ and $R^5$ is hydrogen.

7. A pesticidal composition which comprises: an effective amount of a compound of the formula I, as set forth in claim 1, and at least one solid or liquid carrier.

* * * * *